United States Patent
Pate et al.

(10) Patent No.: US 10,864,193 B2
(45) Date of Patent: Dec. 15, 2020

(54) PARASITICIDAL COMPOSITIONS COMPRISING FIPRONIL AT HIGH CONCENTRATIONS

(71) Applicant: BOEHRINGER INGELHEIM ANIMAL HEALTH USA INC., Duluth, GA (US)

(72) Inventors: James Pate, Hampton, NJ (US); Natalya Shub, Allentown, PA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/522,647

(22) PCT Filed: Oct. 30, 2015

(86) PCT No.: PCT/US2015/058207
§ 371 (c)(1),
(2) Date: Apr. 27, 2017

(87) PCT Pub. No.: WO2016/069983
PCT Pub. Date: May 6, 2016

(65) Prior Publication Data
US 2017/0333397 A1    Nov. 23, 2017

Related U.S. Application Data

(60) Provisional application No. 62/073,190, filed on Oct. 31, 2014.

(51) Int. Cl.
| | |
|---|---|
| A61K 31/415 | (2006.01) |
| A61K 31/215 | (2006.01) |
| A01N 43/56 | (2006.01) |
| A01N 47/02 | (2006.01) |
| A01N 49/00 | (2006.01) |
| A01N 43/40 | (2006.01) |
| A61K 9/00 | (2006.01) |

(52) U.S. Cl.
CPC .............. *A61K 31/415* (2013.01); *A01N 43/40* (2013.01); *A01N 47/02* (2013.01); *A01N 49/00* (2013.01); *A61K 9/0017* (2013.01); *A61K 31/215* (2013.01); *A01N 43/56* (2013.01)

(58) Field of Classification Search
CPC ..... A61K 31/415; A61K 31/215; A01N 43/56
See application file for complete search history.

(56) References Cited

U.S. PATENT DOCUMENTS

| | | |
|---|---|---|
| 8,653,128 B1 | 2/2014 | Taneja |
| 2005/0192319 A1 | 9/2005 | Boeckh et al. |

FOREIGN PATENT DOCUMENTS

WO        2010/106325 A1    9/2010

OTHER PUBLICATIONS

Material Safety Data Sheet for Frontline Plus for Cats/ Frontline Plus for Dogs, Merial/Ancare, published Sep. 10, 2013, downloaded Jul. 15, 2019 from http://hagarin.co.il/Content/editor/73111036_FrontlinePlusDogMSDS.pdf.
European Supplementary Protection Certificate, Marketing Authorisation No. Vm 15052/4063, for Duoflect spot-on solution for dogs and cats, Ceva Animal Health, originally published May 7, 2014.

*Primary Examiner* — Samira J Jean-Louis
(74) *Attorney, Agent, or Firm* — John Ezcurra; Judy Jarecki-Black

(57) ABSTRACT

The invention provides for spot-on formulations comprising fipronil in a high concentration for the treatment or prophylaxis of parasites of mammals and birds, and in particular, cats, dogs, horses, chickens, sheep and cattle with the aim of ridding these animals of all the parasites commonly encountered by birds and mammals. The invention also provides for effective and lasting destruction of ectoparasites, such as fleas, ticks, itch mites and lice, and of endoparasites, nematodes, such as filariae, and roundworms of the digestive tract of animals and humans.

8 Claims, No Drawings

PARASITICIDAL COMPOSITIONS COMPRISING FIPRONIL AT HIGH CONCENTRATIONS

This application claims benefit of priority to U.S. Provisional Patent Application Ser. No. 62/073,190 filed Oct. 31, 2014 and incorporated herein by reference.

FIELD OF THE INVENTION

The present invention provides for topical veterinary compositions comprising fipronil alone in a high concentration (>10% w/v), or fipronil at a high concentration in combination with at least one second active agent, such as, for example an insect growth regulator (IGR) active agent and optionally at least one crystallization inhibitor in an organic solvent for controlling ectoparasites in animals; the use of these compositions against ectoparasites, and methods for preventing or treating parasitic infections and infestations in animals. In certain embodiments where the compositions contain an endoparasiticidal active agent in addition to fipronil, the compositions and methods will also be effective at controlling endoparasites that harm animals.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

BACKGROUND OF THE INVENTION

Animals such as mammals and birds are often susceptible to parasite infestations/infections. These parasites may be ectoparasites, such as insects and arachnids, and endoparasites such as filariae and other worms. Domesticated animals, such as cats and dogs, are often infested with one or more of the following ectoparasites:

fleas (e.g. *Ctenocephalides* spp., such as *Ctenocephalides felis* and the like), ticks (e.g. *Rhipicephalus* spp., *Ixodes* spp., *Dermacentor* spp., *Amblyomma* spp., and the like), mites (e.g. *Demodex* spp., *Sarcoptes* spp., *Otodectes* spp., and the like), lice (e.g. *Trichodectes* spp., *Cheyletiella* spp., *Linognathus* spp. and the like), mosquitoes (*Aedes* spp., *Culex* spp., *Anopheles* spp. and the like) and flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas are also vectors of pathogenic agents in animals and humans, such as dog tapeworm (*Dipylidium caninum*).

Similarly, ticks are also harmful to the physical and psychological health of the animal or human. However, the most serious problem associated with ticks is that they are the vector of pathogenic agents in both humans and animals. Major diseases which are caused by ticks include borreliosis (Lyme disease caused by *Borrelia burgdorferi*), babesiosis (or piroplasmosis caused by *Babesia* spp.) and rickettsiosis (also known as Rocky Mountain spotted fever). Ticks also release toxins which cause inflammation or paralysis in the host animal. Occasionally, these toxins are fatal to the host.

Likewise, farm animals are also susceptible to parasite infestations. For example, cattle are affected by a large number of parasites. A parasite which is very prevalent among farm animals is the tick genus *Boophilus*, especially those of the species *microplus* (cattle tick), *decoloratus* and *annulatus*. Ticks, such as *Boophilus microplus*, are particularly difficult to control because they live in the pasture where farm animals graze.

Animals and humans also suffer from endoparasite infections including, for example, helminthiasis which is most frequently caused by a group of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*

1-arylpyrazoles as a class of compounds that are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2005/0182048; US 2006/0135778; US 2008/0132487; US 2008/0031902; U.S. Pat. Nos. 4,963, 575; 5,122,530; 5,232,940; 5,236,938; 5,246,255; 5,547, 974; 5,567,429; 5,576,429; 5,608,077; 5,714,191; 5,814, 652; 5,885,607; 5,567,429; 5,817,688; 5,885,607; 5,916, 618; 5,922,885; 5,994,386; 6,001,384; 6,010,710; 6,057, 355; 6,069,157; 6,083,519; 6,090,751; 6,096,329; 6,124, 339; 6,180,798; 6,335,357; 6,350,771; 6,372,774; 6,395, 906; 6,413,542; 6,685,954; and 7,468,381. See also: EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

These compounds are described as having activity against a very large number of parasites, including insects and arachnids in fields as varied as agriculture, public health and veterinary medicine. The general teaching of these documents indicates that these active compounds may be administered via different routes: oral, parenteral, percutaneous and topical routes. Topical administration comprises, in particular, skin solutions (pour-on or spot-on), sprays, baths, showers, jets, powders, greases, shampoos, creams, etc. The pour-on type skin solutions may be designed for percutaneous delivery or for distribution of the active on the exterior of the animal. Other methods of formulating antiparasitic agents include spot-on formulations.

Spot-on formulations are well known techniques for topically delivering an antiparasitic agent to a limited area of the animal. For example, U.S. Pat. No. 5,045,536 describes such formulations for ectoparasites. Moreover, it is generally known in the art to formulate avermectin and milbemycin derivatives as spot-on formulations. See, e.g. U.S. Pat. No. 5,045,536; EP 677,054; U.S. Pat. No. 5,733,877; U.S. Pat. No. 5,677,332; U.S. Pat. No. 5,556,868; and U.S. Pat. No. 5,723,488. However, as discussed in U.S. Pat. No. 5,045,536, a large number of solvent systems described in the art provide formulations for localized topical application which cause irritancy or toxicity to the host. Hence, there is a need in the art both for more effective and less irritant or toxic formulations.

U.S. Pat. No. 6,395,765 describes certain spot-on compositions comprising the 1-arylpyrazole compound fipronil in combination with a solvent, a co-solvent and a crystallization inhibitor. U.S. Pat. No. 7,759,381 describes certain 1-arylpyrazole compounds that are substituted at the 5-position of the pyrazole ring with alkyl or $C_1$-$C_4$ haloalkyl groups (both patents incorporated by reference in their entirety). These compounds were also found to be particularly effective against fleas and ticks.

U.S. Pat. Nos. 6,096,329 and 6,685,954, both incorporated herein by reference, describe synergistic combinations of 1-arylpyrazole compounds and an Insect Growth Regulator (IGR) active agent, such as (S)-methoprene that are highly efficacious against ectoparasites.

A Summary of Product Characteristics for a product named FIPROSPOT DUO was issued in May 2014 by the European Medicines Agency (EMA) describing a spot-on solution for dogs containing 240 mg fipronil, 120 mg (S)-methoprene. The excipients butylhydroxyanisole and butylhydroxytoluene, diethyleneglycol monoethyl ether and ethanol are also listed in paragraph 6.1. However, no crystallization inhibitors are included in the document.

While it is known in the art that increasing the concentration of fipronil in topical formulations may increase the efficacy of the duration of the topical formulation to combat parasites, these topical formulations do not always provide a satisfactory result because among other things the tendency of fipronil to crystallize out of solution after application to the surface of the animal (e.g., hair coat and skin) thereby creating aesthetic and safety concerns. Hence, notwithstanding the compositions comprising arylpyrazole active agents alone or in combination with other active agents described in the documents above, there is a need for veterinary compositions and methods with improved efficacy and spectrum of coverage to protect animals against both endoparasites and ectoparasites.

Citation or identification of any document in this application is not an admission that such document is available as prior art to the present invention.

SUMMARY OF THE INVENTION

The invention provides for topical formulations, such as spot-on or pour-on formulations, for the treatment or prophylaxis of parasites of mammals and birds, and in particular, cats, dogs, horses, chickens, sheep and cattle with the aim of ridding these animals of all the parasites commonly encountered by birds and mammals. The invention also provides for effective and long-lasting elimination and control of ectoparasites, such as fleas, ticks, itch mites and lice. When used in combination with an active agent that is active against endoparasites, the methods and compositions of the invention will control endoparasites, such as nematodes, filariae such as heartworm, and roundworms of the digestive tract of animals and humans.

In particular this invention provides for topical formulations, such as spot-on or pour-on formulations for treating or preventing a parasitic infection or infestation in an animal comprising: (a) fipronil, (b) optionally a crystallization inhibitor (c) optionally, an organic co-solvent (d) an organic solvent, and (e) optionally, an antioxidant.

The present invention also provides for an easy method of treating parasitic infections and infestations of animals (either wild or domesticated), including livestock and companion animals such as cats, dogs, horses, chickens, sheep, goats, pigs, turkeys and cattle, with the aim of ridding these animals of parasites commonly encountered by such animals. In preferred embodiments, the topical veterinary composition of the invention are advantageously in the form of a spot-on or a pour-on formulation for application to localized areas on the animal to be treated.

The invention also provides methods for the treatment or prevention of parasitic infections and infestations in animals, comprising administering an effective amount of a composition comprising fipronil at a high concentration alone or in combination with an insect growth regulator (IGR) active agent and at least one crystallization inhibitor, optionally in combination with one or more additional active agents. Surprisingly, it has been found that the inventive compositions and formulations described herein exhibit superior broad spectrum efficacy against harmful ectoparasites for a longer duration while still avoiding fipronil from crystallizing out on the skin and/or hair coat of the animal after application when compared to other compositions known in the art. Hence the present invention further provides for topical veterinary compositions and formulations that are effective against ecto- and/or endoparasites for a long period of time (e.g., from 1 to 2 months) while still not crystallizing out upon the skin and/or hair coat of the animal after application.

This invention further provides for topical veterinary compositions and formulations that exhibit better aesthetic appeal to the consumer after application to the skin and/or hair coat of the animal (e.g., lower presence of deposits of active agent on the skin and/or hair coat, or reduced amount of oiliness/wetness, and a more dry appearance) in the first 24 hours after application.

In one embodiment, the invention provides topical veterinary compositions comprising an effective amount of fipronil (Formula Ia) optionally in combination with at least one insect growth regulator (IGR) active agent, optionally at least one crystallization inhibitor and a pharmaceutically or veterinarily acceptable liquid carrier.

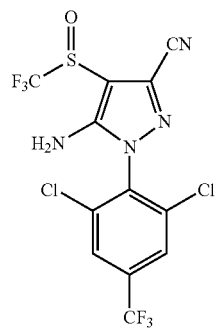

(IA)

In other preferred embodiments, the compositions and methods of the invention comprise the IGR active agents (S)-methoprene, pyriproxyfen, hydroprene, cyromazine, fluazuron, lufenuron, or novaluron.

In one embodiment, the crystallization inhibitor is a combination of a film-forming polymer and a non-ionic surfactant.

In other embodiments the crystallization inhibitor is polyvinylpyrrolidone, copolymers of vinyl acetate and vinylpyrrolidone, a polyethylene glycol, polyoxyethylenated sorbitan esters, a polyoxyethylene castor oil, a polyoxyethylene hydrogenated castor oil, or mixtures thereof.

In one embodiment, the compositions comprise a crystallization inhibitor that may be selected from the polymeric crystallization inhibitors, anionic surfactants, cationic surfactants, non-ionic surfactants, amine salts, amphoteric surfactants, or a mixture thereof, described herein.

In some embodiments the antioxidant is BHA or BHT. In another embodiment the antioxidant is a combination of BHA and BHT.

In some embodiments, the topical veterinary composition of the invention may comprise a $C_1$-$C_{10}$ alcohol or ester, a $C_{10}$-$C_{18}$ saturated fatty acid or esters, a $C_{10}$-$C_{18}$ monounsaturated fatty acid or ester, a monoester or diester of an aliphatic diacid, a glycerol monoesters, a glycerol diester, a glycerol triester, a glycol, a glycol ether, a glycol ester, a glycol carbonate, a polyethylene glycol, a polyethylene glycol monoether, a polyethylene glycol diether, a polyethylene glycol monoester, a polyethylene glycol diester, or a mixture thereof as components in the pharmaceutically or veterinarily acceptable carrier or diluent. In other embodiments, the compositions may include acetone, acetonitrile, benzyl alcohol, ethanol, isopropanol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof in the pharmaceutically or veterinarily acceptable carrier or diluent.

In an embodiment, the invention provides a topical veterinary composition comprising about 10% to about 25% w/v fipronil; about 1% to about 25% w/v of a crystallization inhibitor which is polyvinylpyrrolidone, copolymers of vinyl acetate and vinylpyrrolidone, polyoxyethylenated sorbitan esters, or mixtures thereof; optionally, an organic co-solvent selected from the group consisting of methanol, ethanol, n-propanol, n-butanol and isopropanol; an organic solvent which is acetone, acetonitrile, benzyl alcohol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monomethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof; optionally, about 0.01% to about 2.0% of an antioxidant wherein the organic solvent (as referenced above) is present in the overall composition in a proportion representing the compliment to 100% of the composition; and, wherein, when present, the w/w ratio of the organic co-solvent to organic solvent is between 1/15 and 1/2.

In a further embodiment, the topical veterinary composition further comprises a crystallization inhibitor which is a combination of polyvinylpyrrolidone and polyoxyethylene (20) sorbitan monooleate. In an embodiment of the invention, the topical veterinary composition comprises a polyvinylpyrrolidone which is present in the amount from about 5% to about 15% w/v and the polyoxyethylene (20) sorbitan monooleate is present in the amount from about 5% to about 15% w/v. In another embodiment, the topical veterinary composition further comprises a polyvinylpyrrolidone is present in the amount from about 5% to about 10% w/v and the polyoxyethylene (20) sorbitan monooleate is present in the amount from about 5% to about 11% w/v. In another embodiment, the topical veterinary composition further comprises an organic solvent which is diethylene glycol monoethyl ether and organic co-solvent is ethanol. In a further embodiment, the topical veterinary composition further comprises an antioxidant which is BHA and/or BHT.

In an embodiment, the invention provides a topical veterinary composition comprising about 15% to about 20% w/v fipronil; about 7-13% w/v (S)-methoprene or pyriproxyfen; about 1% to about 25% w/v a crystallization inhibitor which is polyvinylpyrrolidone, copolymers of vinyl acetate and vinylpyrrolidone, polyoxyethylenated sorbitan esters, or mixtures thereof; optionally, an organic co-solvent selected from the group consisting of methanol, ethanol and isopropanol; an organic solvent which is acetone, acetonitrile, benzyl alcohol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof; optionally, about 0.01% to about 2.0% of an antioxidant wherein the organic solvent (as referenced above) is present in the overall composition in a proportion representing the compliment to 100% of the composition; and, wherein, when present, the w/w ratio of the organic co-solvent to organic solvent is between 1/15 and 1/2. In a further embodiment, the topical veterinary composition further comprises a crystallization inhibitor which is a combination of polyvinylpyrrolidone and polyoxyethylene (20) sorbitan monooleate. In another embodiment, the topical veterinary composition further comprises a polyvinylpyrrolidone is present in the amount from about 5% to about 10% w/w and the polyoxyethylene (20) sorbitan monooleate is present in the amount from about 5% to about 11% w/w. In another embodiment, the topical veterinary composition further comprises an organic solvent which is diethylene glycol monoethyl ether and organic co-solvent is ethanol. In a further embodiment, the topical veterinary composition further comprises an antioxidant which is BHA and or the alternative BHT.

In an embodiment of the invention, the topical veterinary composition comprises a weight:weight ratio of a film-forming polymer to non-ionic surfactant which is present in the amount from about 3:1 to 1:1. In an embodiment, the weight:weight ratio of the film-forming polymer to non-ionic surfactant is about 3:1 to about 2:1. In another embodiment, the ratio of film-forming polymer to non-ionic surfactant is about 2.5:1 to about 1.5:1 or about 2:1 to about 1.5:1. In an embodiment the weight:weight ratio of a film-forming polymer to non-ionic surfactant is 1.8:1. In an embodiment the ratio of a film-forming polymer to non-ionic surfactant is 1.7:1. In an embodiment the ratio of a film-forming polymer to non-ionic surfactant is 1.6:1. In an embodiment the ratio of a film-forming polymer to non-ionic surfactant is 1.5:1. In an embodiment the ratio of a film-forming polymer to non-ionic surfactant is 1.4:1. In an embodiment the ratio of a film-forming polymer to non-ionic surfactant is 1.3:1. In an embodiment the ratio of a film-forming polymer to non-ionic surfactant is 1.2:1. In an embodiment the ratio of a film-forming polymer to non-ionic surfactant is 1.1:1. In an embodiment the ratio of a film-forming polymer to non-ionic surfactant is 1:1.

In another embodiment of the invention, the topical veterinary composition comprises a weight:weight ratio of a non-ionic surfactant to a film-forming polymer which is present in the amount from about 3:1 to 1:1. In an embodiment, the weight:weight ratio of the non-ionic surfactant to film-forming polymer is about 3:1 to about 2:1. In another embodiment, the ratio of non-ionic surfactant to film-forming polymer is about 2.5:1 to about 1.5:1 or about 2:1 to about 1.5:1. In an embodiment the ratio of a non-ionic surfactant to a film-forming polymer is 1.8:1. In an embodiment the ratio of a non-ionic surfactant to a film-forming polymer is 1.7:1. In an embodiment the ratio of a non-ionic surfactant to a film-forming polymer is 1.6:1. In an embodiment the ratio of a non-ionic surfactant to a film-forming polymer is 1.5:1. In an embodiment the ratio of a non-ionic surfactant to a film-forming polymer is 1.4:1. In an embodiment the ratio of a non-ionic surfactant to a film-forming polymer is 1.3:1. In an embodiment the ratio of a non-ionic surfactant to a film-forming polymer is 1.2:1. In an embodiment the ratio of a non-ionic surfactant to a film-forming polymer is 1.1:1.

In certain embodiments, the film-forming polymer is polyvinylpyrrolidone, a copolymer of vinyl acetate and vinyl pyrrolidone or a polyethylene glycol, or a combination thereof; and the non-ionic surfactant is a polyoxyethylene sorbitan ester, a polyoxyethylene castor oil or a polyoxyethylene hydrogenated castor oil, or combinations thereof.

In another embodiment, the topical veterinary composition comprises a crystallization inhibitor which is a combination of polyvinylpyrrolidone and polyoxyethylene (20) sorbitan monooleate.

In an embodiment, the invention provides a method for the treatment or prevention of a parasitic infestation or infection in an animal comprising administering to the animal in need thereof an effective amount of the topical veterinary composition according the foregoing topical veterinary compositions. In a further embodiment, the invention provides a method of treatment wherein the parasite is an ectoparasite. In another embodiment, the invention provides a method of treatment wherein the ectoparasite is a flea or tick. In a further embodiment where the composition comprises an additional parasiticide active against endoparasites, the invention provides a method of treatment wherein the parasite is an endoparasite.

In a related aspect, the invention provides a method of treatment for the treatment or prevention of a parasitic infestation or infection in an animal comprising administering to the animal in need thereof an effective amount of the topical veterinary composition according to the foregoing with minimal crystallization formation over a time period over 0 to 24 hours. In a further embodiment, the time period is from over 0 to 22 hours. In another embodiment, the time period is from over 0 to 8 hours. In an embodiment, the time period is from over 0 to 5 hours. In another embodiment, the time period is from over 0 to 4 hours.

While not wishing to be bound by theory, it is believed that the invention spot-on formulation work by the dose dissolving in the natural oils of the animal's skin, hair coat or feathers. From there, the therapeutic agent(s) distribute around the animal's body through the sebaceous glands of the skin by translocation. The therapeutic agent also remains in the sebaceous glands. Thus, the glands provide a natural reservoir for the therapeutic agent which allows for the agent to be drained back out to the follicles to reapply itself to the skin and hair. This, in turn, provides for longer time periods between application as well as not having to re-administer the dose after the animal becomes wet because of rain, bathes, etc. Moreover, the inventive formulation have the further advantage in self-grooming animals of not being directly deposited of the skin or hair coat where the animals could orally ingest the therapeutic agent, thereby becoming sick or possibly interacting with other therapeutic agent being orally administered.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION OF THE INVENTION

The following detailed description is of example embodiments of the presently claimed invention. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

The present invention provides novel and inventive topical compositions comprising a high concentration of fipronil (>10% w/v), alone or in combination with at least one insect growth regulator (IGR) active agent, optionally at least one crystallization inhibitor, optionally with one or more additional active agents, together with a pharmaceutically or veterinary acceptable carrier or diluent.

The compositions of the invention can be in a variety of forms suitable for different forms of administration including, but are not limited to, oral formulations, injectable formulations, and topical, dermal or subdermal formulations.

In some embodiments of the invention, the compositions are preferably in a form that is suitable for topical administration, which includes spot-on formulations that are applied to a localized area on an animal. Topical pour-on formulations are also encompassed by the invention. These formulations provide surprisingly effective protection of the animals against both ectoparasites and endoparasites for an extended period of time.

In one embodiment, the invention provides topical compositions comprising fipronil in combination with at least one insect growth regulator (IGR) active agent together with a pharmaceutically acceptable carrier or diluent.

In another embodiment, the invention provides topical compositions comprising at least fipronil in combination with at least one insect growth regulator (IGR) active agent, at least one crystallization inhibitor, together with a pharmaceutically acceptable carrier or diluent.

Also provided are methods and uses for the treatment and/or prophylaxis of parasitic infections and infestations of animals, comprising administering an effective amount of a formulation of the invention to the animal.

The invention includes at least the following embodiments of a topical veterinary composition comprising:

An embodiment where the composition comprises about 10% to about 25% w/v fipronil. An embodiment where the composition comprises about 12% to about 20% w/v, about 15% to about 20% w/v, about 15% to about 18% w/v fipronil or about 16% to about 18% w/v. In a preferred embodiment, the compositions of the invention comprise fipronil at a concentration of about 17% w/v.

An embodiment wherein the compositions comprise a crystallization inhibitor that may be selected from the polymeric crystallization inhibitors, anionic surfactants, cationic surfactants, non-ionic surfactants, amine salts, amphoteric surfactants, or a mixture thereof, described herein.

An embodiment wherein the composition comprises a crystallization inhibitor and wherein the crystallization inhibitor is a film-forming polymer or a non-ionic surfactant, or a combination thereof. An embodiment wherein the crystallization inhibitor is polyvinylpyrrolidone, copolymers of vinyl acetate and vinylpyrrolidone, a polyethylene glycol, polyoxyethylenated sorbitan esters, polyoxyethylenated castor oil or polyoxyethylenated hydrogenated castor oil, or mixtures thereof.

An embodiment the composition comprises a crystallization inhibitor in the amount from about 1% to about 25% w/v. An embodiment wherein the composition comprises about 3% to about 20%, about 5% to about 15% or about 10% to about 15% w/v of a crystallization inhibitor.

An embodiment where the crystallization inhibitor is polyvinylpyrrolidone, copolymers of vinyl acetate and vinylpyrrolidone, polyoxyethylenated sorbitan esters, or mixtures thereof.

An embodiment of the invention, wherein the topical veterinary composition comprises a weight:weight ratio of a film-forming polymer to non-ionic surfactant which is present in the amount from about 3:1 to 1:1. In an embodiment, the weight:weight ratio of the film-forming polymer to non-ionic surfactant is about 3:1 to about 2:1. In another embodiment, the ratio of film-forming polymer to non-ionic surfactant is about 2.5:1 to about 1.5:1 or about 2:1 to about 1.5:1. In one embodiment the ratio of a film-forming polymer to non-ionic surfactant is 1.8:1. In an embodiment the ratio of a film-forming polymer to non-ionic surfactant is 1.7:1. In an embodiment the ratio of a film-forming polymer to non-ionic surfactant is 1.6:1. In an embodiment the ratio of a film-forming polymer to non-ionic surfactant is 1.5:1. In an embodiment the ratio of a film-forming polymer to non-ionic surfactant is 1.4:1. In an embodiment the ratio of a film-forming polymer to non-ionic surfactant is 1.3:1. In an embodiment the ratio of a film-forming polymer to non-ionic surfactant is 1.2:1. In an embodiment the ratio of a film-forming polymer to non-ionic surfactant is 1.1:1. In an embodiment the ratio of a film-forming polymer to non-ionic surfactant is 1:1.

Another embodiment of the invention, wherein the topical veterinary composition comprises a ratio of a non-ionic surfactant to a film-forming polymer which is present in the amount from about 3:1 to 1:1. In an embodiment, the weight:weight ratio of the non-ionic surfactant to film-forming polymer is about 3:1 to about 2:1. In another embodiment, the ratio of non-ionic surfactant to film-forming polymer is about 2.5:1 to about 1.5:1 or about 2:1 to about 1.5:1. In an embodiment the ratio of a non-ionic surfactant to a film-forming polymer is 1.8:1. In an embodiment the ratio of a non-ionic surfactant to a film-forming polymer is 1.7:1. In an embodiment the ratio of a non-ionic surfactant to a film-forming polymer is 1.6:1. In an embodiment the ratio of a non-ionic surfactant to a film-forming polymer is 1.5:1. In an embodiment the ratio of a non-ionic surfactant to a film-forming polymer is 1.4:1. In an embodiment the ratio of a non-ionic surfactant to a film-forming polymer is 1.3:1. In an embodiment the ratio of a non-ionic surfactant to a film-forming polymer is 1.2:1. In an embodiment the ratio of a non-ionic surfactant to a film-forming polymer is 1.1:1.

In certain embodiments, the film-forming polymer is polyvinylpyrrolidone, a copolymer of vinyl acetate and vinyl pyrrolidone or a polyethylene glycol, or a combination thereof; and the non-ionic surfactant is a polyoxyethylene sorbitan ester, a polyoxyethylene castor oil or a polyoxyethylene hydrogenated castor oil, or combinations thereof.

In another embodiment, the topical veterinary composition comprises a crystallization inhibitor which is a combination of polyvinylpyrrolidone and polyoxyethylene (20) sorbitan monooleate.

Another embodiment where an organic co-solvent is optionally present. An embodiment where the organic co-solvent is present, and is selected from the group consisting of methanol, ethanol, n-propanol, n-butanol and isopropanol. An embodiment of the composition where there is an organic solvent which is acetone, acetonitrile, benzyl alcohol, diisobutyl adipate, diisopropyl adipate, glycerol formal, butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, dimethyl isosorbide, 2-pyrrolidone, N-methylpyrrolidone, diethylene glycol monoethyl ether, triacetin, butyl acetate, octyl acetate, propylene carbonate, butylene carbonate, dimethyl sulfoxide, dimethylformamide, dimethylacetamide, or any combination thereof. The organic solvent is present in the overall composition in a proportion representing the compliment to 100% of the composition; and, wherein, when present, the w/w ratio of the organic co-solvent to organic solvent is between 1/15 and 1/2.

An embodiment where an antioxidant is optionally present in the amount of about 0.01% to about 2.0%.

An embodiment which provides methods for the treatment or prevention of parasitic infections and infestations in an animal comprising administering an effective amount of a composition comprising fipronil at a high concentration (>10% w/v) optionally in combination with at least one insect growth regulator (IGR) active agent, optionally at least one crystallization inhibitor, optionally in combination with an additional active agent, together with a pharmaceutically acceptable carrier, or pharmaceutically acceptable salts, solvates or hydrates thereof, together with a pharmaceutically acceptable carrier or diluent.

In one embodiment, the compositions comprise a crystallization inhibitor that may be selected from the polymeric crystallization inhibitors, anionic surfactants, cationic surfactants, non-ionic surfactants, amine salts, amphoteric surfactants, or a mixture thereof, described herein.

In another embodiment the composition comprises a crystallization inhibitor which is a combination of polyvinylpyrrolidone and polyoxyethylene (20) sorbitan monooleate. In another embodiment, the topical veterinary composition comprises a polyvinylpyrrolidone which is present in the amount from about 5% to about 15% w/v and the polyoxyethylene (20) sorbitan monooleate is present in the amount from about 5% to about 15% w/v. In a further embodiment, the polyvinylpyrrolidone is present in the amount from about 5% to about 10% w/v and the polyoxyethylene (20) sorbitan monooleate is present in the amount from about 5% to about 11% w/v.

In one embodiment, the composition comprises an organic solvent which is diethyleneglycol monoethyl ether, propylene carbonate or benzyl alcohol. In another embodiment, the organic solvent is diethyleneglycol monoethyl ether.

In embodiment of the composition the organic solvent is diethylene glycol monoethyl ether and organic co-solvent is ethanol.

In embodiment of the composition the antioxidant is BHA and or the alternative BHT.

In another embodiment of the composition, the composition comprises fipronil in combination with one or more additional active agents. In an embodiment of the composition, the second active agent is an insect growth regulator, a neonicotinoid, an avermectin, milbemycin, a cyclic depsipeptide, an anthelmintic active agent, an amino acetonitrile active agent, isoxazoline active agent, or an aryloazol-2-yl cyanoethylamino active agent.

It is also noted that in this disclosure and in the claims and/or paragraphs, the compounds of the invention are intended to include all stereoisomers and crystalline forms (which includes hydrated forms, polymorphic forms and amorphous forms with up to 15% by weight crystalline structure) thereof.

Definitions

Terms used herein will have their customary meaning in the art unless specified otherwise. The organic moieties mentioned in the definitions of the variables of formula (I) or (IA) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. Animals include, but are not limited to, humans, cats, dogs, cattle, chickens, cows, deer, goats, horses, llamas, pigs, sheep and yaks. It also includes an individual animal in all stages of development, including embryonic and fetal stages.

The expression "effective amount" as used herein means a concentration of the active agent in the composition sufficient to elicit the desired biological response to the target parasite(s) after administration of the composition to the animal, as measured by methods known in the art and/or described in the examples herein. In some embodiments, an "effective amount" of the active agent in the composition will provide an efficacy of at least 70% against the target parasite compared to an untreated control. In other embodiments, "an effective amount" of the active agent will provide an efficacy of at least 80%, or at least 85% compared to untreated controls. More typically, "an effective amount" of the active agent will provide an efficacy of at least 90%, at least 93%, at least 95% or at least 97% against the target parasite. In certain embodiments, including the prevention of *Dirofilaria immitis,* the term "effective amount" may provide efficacy as high as 100%.

The term "minimal" as used herein refers to an aesthetically acceptable cosmetic appearance with respect to the application of the treatment to the animal. For example, a quantitative scale has been constructed by visual determination to evaluate the amount of crystallization deposits, the oiliness/wetness of the hair coat, and the dryness or lackluster appearance of the hair coat. This visual determination is described in the examples in more detail and summarized in Tables 2, 4, and 5 in the present application. In some embodiments, minimal crystallization refers to a score 2.0 or better as determined by visual inspection on a scale of 0 to 3 in 0.25 increments where 0 represents no presence of crystallization.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl "Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O— (e.g., —OR), wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkyl sulfinyl, haloalkenyl sulfinyl, haloalkynyl sulfinyl, alkyl sulfonyl, alkenyl sulfonyl, alkynyl sulfonyl, haloalkyl-sulfonyl, haloalkenyl sulfonyl, haloalkynyl sulfonyl, alkylamino, alkenylamino, alkynylamino, di(alkyl)amino, di(alkenyl)-amino, di(alkynyl) amino, or trialkylsilyl.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Alkoxycarbonyl refers to —C(=O)—O-alkyl (e.g., ester), wherein alkoxy is as defined above;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$))

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

1-arylpyrazoles as a class of chemicals are well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2008/0132487 and US 2008/0031902; U.S. Pat. Nos. 4,963,575; 5,122,530; 5,232,940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381, 7,517,877, and 7,514,561; and European Patent Publications Nos. EP 0 234 119, EP 0 295 117, EP 0 352 944, EP 0 500 209, EP 0 780 378, EP 0 846 686, and EP 0 948 485, all of which are incorporated herein by reference in their entirety.

The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective against pests, including fleas and ticks.

In one embodiment, the invention provides compositions that comprise at least one 1-arylpyrazole compound of formula (I):

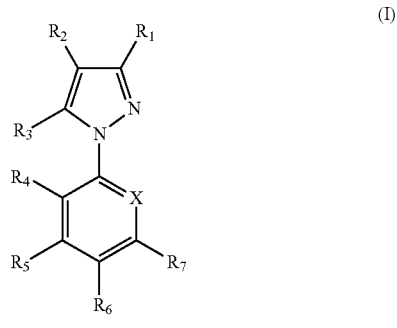

(I)

wherein:

$R_1$ is hydrogen, cyano, nitro, halogen, $R_3$, $R_8$, formyl, —C(O)$R_8$, —C(O)O$R_8$, —C(O)N$R_9R_{10}$, —C(=NOH)NH$_2$, —C(=NNH$_2$)$R_9$, or —C(S)NH$_2$;

$R_2$ is $R_8$, halogen, cyano, nitro, —SCN, 4-5-dicyanoimidazol-2-yl, or —S(O)$_m R_{11}$;

$R_3$ is hydrogen, halogen, alkyl, haloalkyl, OH, O$R_8$, S(O)$_m R_{11}$, —C(O)$R_8$, —C(O)O$R_8$, N$R_9R_{10}$, —N=C($R_9$)($R_{14}$), —N=C($R_{10}$)—Z—($R_9$), —N=C($R_{10}$)—N$R_9R_{10}$, —N($R_8$)—C($R_{10}$)=N$R_9$, —N($R_{11}$)C(O)C$R_{15}R_{10}R_{11}$, —N($R_{11}$)C(O)aryl, —N($R_{11}$)C(O)heteroaryl or —N($R_{11}$)C(O)O$R_{10}$;

$R_4$, $R_5$ and $R_7$ are independently hydrogen, halogen, alkyl, haloalkyl, CN or NO$_2$;

$R_6$ is halogen, alkyl, haloalkyl, alkoxy, haloalkyloxy, cyano, nitro, —C(O)$R_{12}$, —S(O)$_n R_{12}$ or SF$_5$;

X is a nitrogen atom or C—$R_{13}$;

Z is O, S(O)$_m$ or N$R_9$;

$R_8$ is alkyl or haloalkyl;

$R_9$ is hydrogen, alkyl, haloalkyl or alkoxy;

$R_{10}$ is hydrogen, alkyl, haloalkyl, alkoxy, or —C(O)$R_8$;

$R_{11}$ is alkyl, haloalkyl, alkenyl, haloalkenyl, alkynyl, haloalkynyl, alkoxyalkyl, or haloalkoxyalkyl;

$R_{12}$ is alkyl or haloalkyl;

$R_{13}$ is hydrogen, halogen, cyano, nitro, alkyl, haloalkyl, alkoxy or haloalkoxy;

$R_{14}$ is optionally substituted aryl or optionally substituted heteroaryl;

$R_{15}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkyl sulfonyl, haloalkylsulfonyl, alkylamino, dialkylamino, haloalkylamino, di(haloalkyl)amino, aryloxy or arylalkoxy;

wherein said alkyl, haloalkyl, alkoxy, groups are optionally substituted with alkyl, haloalkyl, alkoxy, aryl, or heteroaryl; said aryl or heteroaryl groups are optionally substituted with one or more of alkyl, haloalkyl, aryl, halogen, C(O)$R_8$, —C(O)O$R_8$, —C(O)N$R_9R_{10}$, —C(S)NH$_2$, or —S(O)$_m R_{11}$;

m is 0, 1 or 2; and n is 0, 1 or 2; or a pharmaceutically acceptable salt, hydrate or solvate thereof;

optionally in combination with an insect growth regulator compound, and optionally an additional active agent, or pharmaceutically acceptable salts, hydrates or solvates thereof, together with a pharmaceutically acceptable carrier or diluent.

In another embodiment, the invention provides a composition comprising a 1-aryl-alkyl or 5-haloalkylpyrazole of formula (IA) below:

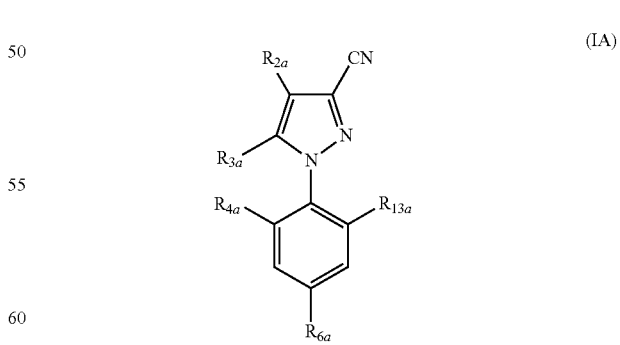

(IA)

or a salt thereof, wherein:

$R_{2a}$ is —S(O)$_m R_{11a}$;

$R_{3a}$ is methyl, ethyl or $C_1$-$C_4$haloalkyl;

$R_{4a}$ is —Cl;

$R_{6a}$ is —CF$_3$;

$R_{13a}$ is —F;

$R_{11a}$ is —$CFCl_2$ or $CF_3$; and m is 0, 1 or 2; optionally in combination with an insect growth regulator; in combination with a pharmaceutically acceptable carrier or diluent.

In a further embodiment of the inventive compositions, the composition will be in the form of a liquid solution or suspension. The pharmaceutically acceptable carrier may be any suitable carrier or diluent commonly used in the formulation art including aqueous or organic solvents or mixtures of solvents. These organic solvents may be found, for example, in Remington Pharmaceutical Sciences, 16$^{th}$ Edition (1986). Organic solvents that can be used in the invention include those described above, and also include but are not limited to: acetyltributyl citrate, oleic acid, fatty acid esters such as the dimethyl ester, diisobutyl adipate, diisopropyl adipate (also known as CERAPHYL 230), ketones including acetone, methylisobutyl ketone (MIK) and methyl ethyl ketone and the like, acetonitrile, benzyl alcohol, methanol, ethyl alcohol, isopropanol, butanol, aromatic ethers such as anisole, butyl diglycol, amides including dimethylacetamide and dimethylformamide, dimethyl sulfoxide, ethylene glycol, propylene glycol, glycol ethers including propylene glycol monomethyl ether, propylene glycol monomethyl ether, dipropylene glycol n-butyl ether, ethylene glycol monoethyl ether, ethylene glycol monomethyl ether, diethylene glycol monoethyl ether, glycol carbonates, monomethylacetamide, dipropylene glycol monomethyl ether, liquid polyoxyethylene glycols (PEG) of different average molecular weight ranges, 2-pyrrolidone including N-methylpyrrolidone, glycerol formal, dimethyl isosorbide, triacetin, $C_1$-$C_{10}$ esters of carboxylic acids such as butyl or octyl acetate, benzyl acetate, aryl esters including benzyl benzoate, ethyl benzoate and the like, propylene carbonate, butylene carbonate, and diethyl phthalate, or a mixture of at least two of these solvents.

These solvents can be supplemented by various excipients according to the nature of the desired phases, such as $C_8$-$C_{10}$ caprylic/capric triglyceride (e.g. ESTASAN® or MIGLYOL® 812), oleic acid or propylene glycol.

In one embodiment of the invention, the pharmaceutically acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, or mixtures thereof.

In some embodiments, the carrier or diluent will comprise a derivative of glycerol including, but not limited to, glycerol monoesters (e.g. monoglycerides), glycerol diesters (e.g. diglycerides), glycerol triesters (e.g. triglycerides such as triacetin), or glycerol formal, or mixtures thereof. Glycerol formal is a mixture of 5-hydroxy-1,3-dioxane and 4-hydroxymethyl-1,3-dioxolane (approximately 60:40), which are cyclic ether compounds derived from glycerol and having 2 oxygen atoms in the ring structure and substituted by alcohol group. Glycerol Formal is a low odor and low toxic solvent for a wide variety of applications in pharmaceutical and cosmetics industry including anti-parasite veterinary formulations.

In another embodiment of the invention, the organic solvents may comprise diisopropyl adipate, dipropylene glycol monomethyl ether, propylene glycol monomethyl ether, 2-pyrrolidone including N-methylpyrrolidone, diethylene glycol monoethyl ether, triacetin, butyl acetate, octyl acetate, propylene carbonate, oleic acid, or a mixture of at least two of these solvents.

In one embodiment, solvents in the composition may include $C_1$-$C_{10}$ esters of carboxylic acids such as butyl or octyl acetate.

In some embodiments of the invention, the carrier comprises dimethyl isosorbide. Dimethyl Isosorbide (DMI) is a high purity solvent and carrier which offers a safe, effective delivery enhancement mechanism for active ingredients in personal care products and pharmaceutical formulations. In addition dimethyl isosorbide is sometimes used as an epidermal penetration enhancer to provide enhanced penetration of active agents to the epidermis. It may also provide delivery of active agents into the skin while avoiding crystallization of the active agent, which will severely limit the effectiveness of the formulation. Dimethyl Isosorbide is soluble in a variety of ingredients including water, cottonseed oil, isopropanol, isopropyl myristate, propylene glycol, polysorbate 20, and polysorbate 80. It is insoluble in hydrogenated castor oil, lanolin, mineral oils or silicone oil (dimethicone).

In other embodiments, the carrier or diluent can comprise dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides, or mixtures thereof.

In some embodiments, the compositions of the invention can be in a variety of forms suitable for different forms of administration including, but are not limited to, oral formulations, injectable formulations, and topical, dermal or subdermal formulations.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. These compositions may be preserved by the addition of an anti-oxidant such as ascorbic acid or other known preservatives.

Aqueous suspensions may contain the active agents in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

In a preferred embodiment of the invention, compositions suitable for topical administration to an animal are provided. Topical, dermal and subdermal formulations can include emulsions, creams, ointments, gels, pastes, powders, shampoos, pour-on formulations, ready-to-use formulations, spot-on solutions and suspensions. Topical application of the inventive compositions can allow for the active agents to be delivered and distributed through the sebaceous glands of the animal or throughout the hair coat and/or allow some active agents to achieve a systemic effect (plasma concentration). When the compound is distributed throughout sebaceous glands, the sebaceous glands can act as a reservoir, whereby there can be a long-lasting, e.g. 1-2 months effect or longer. Cochet and co-workers reported the distribution of fipronil, a 1-arylpyrazole compound, to the stratum corneum, the viable epidermis and the sebaceous glands and epithelial layers of beagle dogs after spot-on administration (see Cochet et al., *Eur. J. Drug Metab. Pharmacokinet.*, 1997, 22(3), 211-216). Using $^{14}$C radiolabeled drug, the publication demonstrated that fipronil is displaced from the point of application and distributed to the whole skin, where it was persistently detected for up to 56 days after treatment.

In preferred embodiment, the compositions of the invention are in the form of a spot-on formulation that is applied to a localized area on an animal, rather than the entire coat of the animal or a large portion of the animal's coat. In one embodiment of a localized region, the location is between the shoulders. The spot-on formulation according to the present invention provide long-lasting and broad-spectrum efficacy against ectoparasites and endoparasites when the solution is applied to the mammal or bird. The spot-on formulations provide for topical administration of a concentrated solution, suspension, microemulsion or emulsion for intermittent application to a spot on the animal, generally between the two shoulders (solution of spot-on type).

Spot-on formulations are well known techniques for topically delivering an antiparasitic agent to a limited area of the animal. For example, U.S. Pat. Nos. 5,045,536; 6,395,765; 6,096,329; 6,426,333; 6,482,425; 6,962,713; and 6,998,131, all incorporated herein by reference, describe spot-on formulations. WO 01/957715, also incorporated herein by reference, describes a method for controlling ectoparasites in small rodents as well as interrupting or preventing the diseases caused by arthropods in small rodents, which comprise applying topical formulations, such as spot-on compositions, to the skin, or hair of the rodents.

For spot-on formulations, the pharmaceutically acceptable carrier may be a liquid carrier vehicle as described herein, and other carriers described in the art, for example in U.S. Pat. No. 6,426,333, which is incorporated herein by reference. In some embodiments, the liquid carrier vehicle can optionally contain a crystallization inhibitor such as the crystallization inhibitors described below, or mixtures thereof, to inhibit the formation of crystals or precipitate of the active components.

The veterinarily acceptable carrier will generally comprise a diluent or vehicle in which the active agents are soluble. It will be apparent to those of skill in the art that the carrier or diluent of the topical compositions must be able to deliver the active agents to the targeted location without the active agents precipitating from solution or forming crystals. In some embodiments, the carrier or diluent of the compositions will be suitable to avoid precipitation or crystallization of the active agents. In other embodiments, the compositions may include a crystallization inhibitor in addition to the carrier or diluent.

In one embodiment of the invention, the carrier for spot-on compositions may comprise diisopropyl adipate, dipropylene glycol monomethyl ether, propylene glycol monomethyl ether, 2-pyrrolidone, N-methylpyrrolidone, diethylene glycol monoethyl ether, triacetin, butyl acetate, octyl acetate, propylene carbonate, oleic acid, or a mixture of at least two of these solvents.

In another embodiment of the invention, the pharmaceutically acceptable carrier of the formulation comprises $C_1$-$C_{10}$ alcohols or esters thereof (including acetates, such as ethyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids , or mixtures thereof.

In yet another embodiment, preferred solvents include $C_1$-$C_{10}$ esters of carboxylic acids such as butyl or octyl acetate.

In another embodiment, the compositions of the invention that are suitable for topical administration will comprise glycerol derived carriers including glycerol monoesters (e.g. monoglycerides), glycerol diesters (e.g. diglycerides), glycerol triesters (e.g. triglycerides such as triacetin), glycerol formal, or mixtures thereof.

In another embodiment, the compositions of the invention for topical administration will comprise an alcohol including ethanol or isopropanol, propylene glycol, dimethyl isosorbide (DMI), 2-pyrrolidone, N-methylpyrrolidone, dimethylsulfoxide, glycerol formal, glycol ethers including diethylene glycol monoethyl ether, diethylene glycol monomethyl ether and the like, or mixtures thereof.

In yet another embodiment, the topical compositions of the invention will comprise glycerol formal, dimethyl isosorbide, N-methylpyrrolidone, diethylene glycol monoethyl ether, or mixtures thereof. In still another embodiment, the topical compositions will comprise glycerol formal, dimethyl isosorbide, or a mixture thereof.

Spot-on formulations, described for example in U.S. Pat. No. 7,262,214 (incorporated herein by reference), may be prepared by dissolving the active ingredients into the pharmaceutically or veterinary acceptable vehicle. Alternatively, the spot-on formulation can be prepared by encapsulation of the active ingredients to leave a residue of the therapeutic agent on the surface of the animal. These formulations will vary with regard to the weight of the therapeutic agent in the combination depending on the species of animal to be treated, the severity and type of infection and the body weight of the animal.

Pour-on formulations are described, for example, in U.S. Pat. No. 6,010,710, which is incorporated herein by reference. Some pour-on formulations are advantageously oily, and generally comprise a diluent or vehicle and also a solvent (e.g. an organic solvent) for the active ingredient if the latter is not soluble in the diluent. Other pour-on formulations may be in hydrophilic carriers such as alcohols (e.g. ethanol or isopropanol and the like) or other water-miscible solvents. Pour-on formulation may be administered to livestock animals such as cattle and sheep. Typically, pour-on formulations are administered to the animal as a stripe to an external surface of the animal, e.g. a stripe from head to tail of the animal. In one embodiment, the process comprises applying the solution to livestock animals before they arrive in the Feed Lot, it being possible for this application to be the final one before the animals are slaughtered.

Typically, the 1-arylpyrazole(s) active agents are present in the formulation at a concentration of about 1 to about 25% (w/v). In some embodiments of the invention, the 1-arylpyrazole(s) active agents are present in the formulation as a concentration from about 1 to about 20% or about 10 to about 20% (w/v). In still another embodiment of the invention, the 1-arylpyrazole active agent(s) are present in the formulation as a concentration about 12 to about 20% (w/v), about 15 to about 20% (w/v), about 15 to about 18% (w/v) or about 16 to about 18% (w/v). In one embodiment, the 1-arylpyrazole(s) active agents are present at a concentration of about 17% (w/v).

In some embodiments, the novel and inventive formulations may typically contain about 1 to about 30% (w/v) of at least one IGR compound. In other embodiments, the formulations will contain about 1 to about 20% (w/v), about 5 to about 15% (w/v) of one or more IGR compounds. More typically, the active agent is present in the formulation as a concentration about 7-13% (w/v) or 8-12% (w/v). In one embodiment, the IGR compound is present in a concentration of about 9% (w/v). In another embodiment, the IGR compound is present in a concentration of about 12% (w/v).

In some embodiments of the invention, an emollient and/or spreading and/or film-forming agent may be added to the topical compositions of the invention. In some embodiments the emollient and/or spreading and/or film-forming agents include:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil;

(b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil);

(c) cationic surfactants such as water-soluble quaternary ammonium salts of formula $N^+R'R''R'''R''''Y^-$, in which the R radicals are optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+R'R''R'''$ in which the R radicals are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine, and (g) a mixture of at least two of these agents.

In one embodiment, the emollient is used in a proportion of from about 0.1 to about 10%, or about 0.25 to about 5% (w/v).

In one embodiment of the invention, the composition can be in ready-to-use solution form as is described, for example, in U.S. Pat. No. 6,395,765, which is incorporated herein by reference. In addition to the active agents, the ready-to-use solution can contain a carrier or diluent, including an organic solvent(s), and a crystallization inhibitor.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). In another embodiment, the crystallization inhibitor may be present in a concentration of about 10% to about 20% (w/v). Acceptable inhibitors are those whose addition to the formulation inhibits the formation of crystals of the active agents when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the 1-arylpyrazole in a solvent as described above with 10% (w/v) of the crystallization inhibitor will result in less 20, preferably less than 10 crystals when placed on a glass slide at 20° C. for 24 hours.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsulfoxide, polyethylene glycols, benzyl alcohol, mannitol, glycerol, sorbitol or polyoxyethylenated esters of sorbitan; lecithin or sodium carboxymethylcellulose; or acrylic derivatives, such as polymers derived from acrylic monomers including polyacrylates or polymethacrylates; and, a solvent as described herein that inhibits the crystallization of the active agent, and similar compounds;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $YY^-$ is an anion of a strong acid, such as halide, sulfate and sulfonate anions; cetyltrimethylammonium bromide is one of the cationic surfactants which can be used;

(d) amine salts of formula $N^+R'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil including polyoxyethylenated castor oil and polyoxyethylenated hydrogenated castor oil, polyglycerol esters, polyoxyethylenated fatty alcohols, polyoxyethylenated fatty acids, polyoxyethylene phytosterol, polyoxyethylene lanolin or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated ester of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The volume of the topical composition applied is not restricted as long as the amount of substance administered is shown to be safe and efficacious. Typically, the volume applied depends on the size and weight of the animal as well as the concentration of active, the extent of infestation by parasites and the type of administration. For spot-on compositions, the volume applied is typically of the order of about 0.1 to about 1 ml, or about 0.1 ml to about 5 ml, or about 0.1 ml to about 10 ml. In other embodiments, the volume may be about 4 ml to about 7 ml. For larger animals, the volume may be higher including, but not limited to, up to 10 ml, up to 20 ml or up to 30 ml, or higher. In one embodiment of the volume, the volume is on the order of about 0.5 ml to about 1 ml or about 0.5 ml to about 2 ml for cats, and on the order of about 0.3 to about 3 ml or 4 ml for dogs, depending on the weight of the animal.

For the pour-on form of the composition, the volume applied can be of the order of about 0.3 to about 100 mL. In other embodiments, volume applied of the pour-on formulations may be about 1 ml to about 100 ml or about 1 ml to about 50 ml. In still other embodiments, the volume may be about 5 ml to about 50 ml or about 10 ml to about 100 ml.

Dosage forms may contain from about 0.5 mg to about 5 g of a combination of active agents. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Methods of Treatment

In another aspect of the invention, a method for preventing or treating a parasite infestation/infection in an animal is provided, comprising administering a composition comprising an effective amount of at least one 1-arylpyrazole compound of formula (I) or (IA) optionally in combination with at least one IGR compound, together with a pharmaceutically acceptable carrier. In some embodiments, the compositions used in the methods of the invention comprise a crystallization inhibitor as described above.

Ectoparasites against which the methods and compositions of the invention are effective include, but are not limited to, fleas, ticks, mites, mosquitoes, flies and lice. The compositions and methods of the invention are also effective against endoparasites when an endoparasiticide is included in the composition including, but not limited to, cestodes, nematodes, such as filariae, *Dirofilaria immitis* (heartworm), hookworms and roundworms of the digestive tract of animals and humans.

In one embodiment of the invention, methods for the treatment or prevention of a parasitic infestation or infection in a domestic animal are provided, which comprise administering a composition comprising an effective amount of at least one arylpyrazole of formula (I) or (IA), at least one IGR compound, and optionally one or more additional active agent to the animal.

In one embodiment, the invention provides methods for the treatment and prevention of parasitic infections and infestations of animals (either wild or domesticated), including livestock and companion animals such as cats, dogs, horses, chickens, sheep, goats, pigs, turkeys and cattle, with the aim of ridding these animals of parasites commonly encountered by such animals.

In a preferred embodiment, the invention provides methods and compositions for the treatment or prevention of parasitic infections and infestations in companion animals including, but not limited to, cats and dogs. In a particularly preferred embodiment of the invention, the methods and compositions described are used to prevent or treat parasitic infections or infestations in cats.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

It will be appreciated by those of skill in the art that the methods of the invention encompass administering the 1-arylpyrazole compound(s), the IGR compound(s) and optionally one or more additional active agent(s) together in the same carrier or diluent or separately where each active agent or mixtures of the active agents are present in their own carriers or diluents. For example when the active agents are administered topically, the 1-arylpyrazole compound(s) may be administered at the same location on the animal at the same time as the other active agents, or the 1-arylpyrazole compound(s) may be administered at a different location on the animal than the other active agents. Each active agent may be administered simultaneously or sequentially in separate carriers, which may be the same or different. Furthermore, each of the active compound(s) may be administered by the same mode of administration (e.g. topical, oral, parenteral, etc.), or the different active agents may be administered by different modes of administration.

In one embodiment of the invention, the method comprises administering each of the 1-arylpyrazole(s), the IGR (s) and optionally one or more additional active agent(s) separately and sequentially.

In another embodiment of the invention, the method comprises administering each of the 1-arylpyrazole(s), the IGR(s) and the optional additional active agent(s) simultaneously.

In yet another embodiment of the invention, the method comprises administering each of the 1-arylpyrazole(s), the IGR(s) and the optional additional active agent(s) simultaneously in the same carrier or diluent.

In still another embodiment, the method comprises administering one or more of the active agents separately from the other active agents in a separate carrier, which may be the same or different than the carrier that is used for the other active agents.

In another aspect of the invention, a kit for the treatment or prevention of a parasitic infestation in an animal is provided, which comprises at least one 1-arylpyrazole(s), at least one IGR(s) and optionally one or more additional active agent(s) together with a pharmaceutically acceptable carrier and a dispensing device for topical application of the composition. The dispensing device may be a pipette, syringes, roll on, droppers, capsules, foil packages, vials, twist tip containers and other single dose and multi-dose containers, which includes an effective dose of each active agent in the pharmaceutically acceptable carrier or diluent.

Additional Active Agents

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and endoparasiticidal agents.

Veterinary pharmaceutical agents that may be included in the compositions of the invention are well-known in the art (see e.g. *Plumb' Veterinary Drug Handbook, 5$^{th}$ Edition*, ed. Donald C. Plumb, Blackwell Publishing, (2005) or *The Merck Veterinary Manual, 9$^{th}$ Edition*, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth sub salicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, di ethyl carb amazine citrate, diethyl stilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levetiracetam, levothyroxine sodium, lidocaine, lincomycin, liothyronine sodium, lisinopril, lomustine (CCNU), lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, a second 1-arylpyrazole compounds such as a 1-phenylpyrazoles known in the art may be combined in the compositions of the invention with fipronil. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference. In addition, the compositions of the invention may include the new avermectin compounds tenvermectin A and tenvermectin B (see "Gene Replacement for the Generation of Designed Novel Avermectin Derivatives with Enhanced Acaricidal and Nematicidal Activities" Huang et al., Applied and Environmental Microbiology, August 2015, vol. 11, no. 16, pp. 5326-5334.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all incorporated herein by reference. Naturally occurring milbemycins are described in U.S. Pat. No. 3,950,360 (incorporated herein by reference) as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In another embodiment of the invention, the compositions may include a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225, 598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR that may be included in the composition is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3(2H)-one. In a particularly preferred embodiment, the compositions of the invention comprise methoprene or pyriproxyfen.

In another embodiment, the compositions of the invention may include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and synthetic pyrethroids. Pyrethroids are synthetic analogs of the pyrethrins with increased potency and stability. Pyrethroids that may be used in the compositions of the invention include, but are not limited to, permethrin, alphacypermethrin, cyfluthrin, beta-cyfluthrin, cyhalothrin, cypermethrin, cyphenothrin, deltamethrin, fenvalerate, flucythrinate, flumethrin, tau-fluvalinate, allethrin, bioaltherin, phenothrin, resmethrin, tetramethrin, transfluthrin and etofenprox. Carbamate insecticides include, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the compositions of the invention may include one or more anti-nematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include anti-trematodal agents. Suitable anti-trematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlophalan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874). An antiparasitic agent that can be combined with the compound of the invention to form a composition can be a biologically active peptide or protein including, but not limited to, cyclic depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86). In another embodiment, the cyclic depsipeptide will be PF1022A or a derivative thereof.

In another embodiment, the compositions of the invention may comprise an active agent from the neonicotinoid class of active agents. The neonicotinoids bind and inhibit insect specific nicotinic acetylcholine receptors. In one embodiment, the neonicotinoid insecticidal agent that may be included in a composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060.

In another embodiment, the compositions of the invention may comprise nitenpyram, another active agent of the neonicotinoid class of pesticides. Nitenpyram has the following chemical structure and is the active ingredient in the oral product CAPSTAR™ Tablets sold by Novartis Animal Health.

In certain embodiments, an insecticidal agent that can be combined with the compositions of the invention is a semicarbazone, such as metaflumizone.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the compositions of the invention. These compounds are described, for example, in WO 2004/024704 and U.S. Pat. No. 7,084,280 (both incorporated by reference); Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In another particularly preferred embodiment, the compositions of the invention may advantageously include one or more compounds of the isoxazoline class of compounds including, but not limited to afoxolaner, fluralaner and sarolaner. These active agents are described in WO 2007/079162, WO 2007/075459 and US 2009/0133319, WO 2007/070606 and US 2009/0143410, WO 2009/003075, WO 2009/002809, WO 2009/024541, U.S. Pat. No. 7,662,972, WO 2008/122375, WO 2010/003877, WO 2010/003923, WO 2009/025983, WO 2008/150393, WO 2008/154528, WO 2009/045999, WO 2009/051956, WO 2009/126668, WO 2009/0259832, WO 2008/109760, US 2009/0156643, US 2010/0144797, US 2010/0137612, US 2011/009438, U.S. Pat. No. 8,466,115, U.S. Pat. No. 7,662,972, U.S. Pat. No. 7,964,204, U.S. Pat. No. 8,410,153 and WO 2011/075591, all of which are incorporated herein by reference in their entirety.

In general, the additional active agent is included in the composition in an amount of between about 0.1 µg and about 1000 mg. More typically, the additional active agent may be included in a dose of about 10 µg to about 500 mg, about 1 mg to about 300 mg, about 10 mg to about 200 mg or about 10 mg to about 100 mg. In one embodiment of the invention, the additional active agent is included in a dose of between about 1 µg and about 10 mg. In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In another embodiment, the dose will be about 1 mg/kg to about 10 mg/kg, about 2 mg/kg to about 8 mg/kg or about 2 mg/kg to about 6 mg/kg. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The compositions of the invention are made by mixing the appropriate amount of the active agents, pharmaceutically acceptable carrier or diluent and optionally a crystallization inhibitor, antioxidant, preservative, film former, etc., to form a composition of the invention. Various forms (e.g. tablets, pastes, pour-on, spot-on, collars, etc.) of the composition can be obtained by following the method of making these forms described above by the description of making these forms found in general formulation text known to those in the art, e.g. *Remington—The Science and Practice of Pharmacy* (21$^{st}$ Edition) (2005), *Goodman & Gilman's The Pharmacological Basis of Therapeutics* (11$^{th}$ Edition) (2005) and *Ansel's Pharmaceutical Dosage Forms and Drug Delivery Systems* (8$^{th}$ Edition), edited by Allen et al., Lippincott Williams & Wilkins, (2005).

The inventive formulations may contain other inert ingredients such as antioxidants, preservatives, or pH stabilizers. These compounds are well known in the formulation art. Antioxidant such as an alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, with about 0.05 to about 1.0% being especially preferred.

Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

The compositions of the invention are administered in parasiticidally effective amounts which are determined by the route of administration, e.g. oral, parenteral, topical, etc. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific animal and parasite.

In one treatment embodiment, the treatment is carried out so as to administer to the animal, on a single occasion, a dose containing between about 0.001 and about 100 mg/kg of body weight of the active agents. In another embodiment, the composition administered delivers a dose of about 1 to 20 mg/kg of an arylpyrazole, about 1 to 20 mg/kg of an IGR. In embodiments where an additional active agent is present, the composition may be prepared to deliver a dose of about 0.01 to 5 mg/kg of a macrocyclic lactone active agent, and about 1 to 20 mg/kg of an anthelmintic compound. In a preferred embodiment, the compositions of the invention will deliver about 5 to 15 mg/kg of an arylpyrazole including fipronil, about 5 to 15 mg/kg of an IGR including methoprene and pyriproxyfen. In another embodiment, the compositions will deliver a dose of 10-15 mg/kg of fipronil and 5-10 mg/kg of methoprene or pyriproxyfen.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal.

The solutions according to the invention may be applied using any means known per se, e.g. using an applicator gun or a metering flask, pipette, syringes, roll on, droppers, capsules, foil packages, vials, twist tip containers and other single dose and multi-dose containers.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm$^2$ or larger. In another embodiment of the invention, the localized region has a surface are of between about 5 and about 10 cm$^2$ area.

EXAMPLES

The invention is further described by the following non-limiting examples which further illustrate the invention, and are not intended, nor should they be interpreted to, limit the scope of the invention.

Example 1

Compositions of the Invention Containing a High Concentration of Fipronil and Crystallization Inhibitors Tables 1 and 2 below list certain non-limiting topical veterinary compositions of the invention that were prepared.

TABLE 1

| Ingredient | Concentration % w/w | | | | | |
|---|---|---|---|---|---|---|
| | 1 | 2 | 3 | 4 | 5 | 6 |
| Fipronil | 17.0 | 17.0 | 17.0 | 17.0 | 17.0 | 17.0 |
| (S)-Methoprene | 8.82 | 8.82 | 8.82 | 8.82 | 8.82 | 8.82 |
| Transcutol P/ethanol | QS 100% [10% v/v ethanol in Transcutol P] | | | | | |
| Polysorbate 80 | 4.90 | 10.0 | 7.5 | 9.0 | 6.0 | 9.0 |
| PVP[1] | 4.90 | 6.0 | 7.5 | 6.0 | 9.0 | 9.0 |
| BHA | 0.02 | 0.02 | 0.02 | 0.02 | 0.02 | 0.02 |
| BHT | 0.01 | 0.02 | 0.02 | 0.02 | 0.01 | 0.01 |

| Ingredient | Concentration % w/w | | | | | |
|---|---|---|---|---|---|---|
| | 7 | 8 | 9 | 10 | 11 | 12 |
| Fipronil | 17.0 | 17.0 | 17.0 | 17.0 | 17.0 | 17.0 |
| (S)-Methoprene | 8.82 | 8.82 | 8.82 | 8.82 | 8.82 | 8.82 |
| Polysorbate 80 | 6.0 | 5.0 | 5.0 | 6.0 | 3.0 | 1.0 |
| PVP | 6.0 | 9.0 | 10.0 | 11.0 | 6.0 | 6.0 |
| BHA | 0.02 | 0.02 | 0.02 | 0.02 | 0.02 | 0.02 |
| BHT | 0.02 | 0.02 | 0.02 | 0.02 | 0.02 | 0.02 |
| Transcutol P/ethanol | QS 100% [10% v/v ethanol in Transcutol P] | | | | | |

[1]polyvinylpyrrolidone

TABLE 2

| Ingredient | Concentration % w/v | | | | |
|---|---|---|---|---|---|
| Fipronil | 17 | 17 | 17 | 17 | 17 |
| (S)-Methoprene | 8.5 | 8.5 | 8.5 | 8.5 | 8.5 |
| Ethanol | 10 | 10 | 10 | 10 | 10 |
| Polysorbate 80 | 7.5 | 7.5 | 7.5 | 7.0 | 7.0 |
| PVP | 7.5 | 8.0 | 8.5 | 8.0 | 7.75 |
| Transcutol P | QS 100% | | | | |

| Ingredient | Concentration % w/v | | | |
|---|---|---|---|---|
| Fipronil | 17 | 17 | 17 | 17 |
| (S)-Methoprene | 8.5 | 8.5 | 8.5 | 8.5 |
| Ethanol | 7.9 | 7.9 | 9.0 | 9.0 |
| Polysorbate 80 | 7.5 | 7.0 | 7.5 | 7.0 |
| PVP | 7.5 | 8.0 | 7.5 | 8.0 |
| Transcutol P | QS 100% | | | |

The present invention provides composition and methods for treating or preventing a parasitic infection or infestation in an animal with either minimal or no crystal formation which forms as the solvent evaporates after application of the high fipronil composition (over 10 w/w%) on the hair coat of the animal. Applicants observed that the unacceptable levels of crystal formation created unsatisfactory aesthetics. Applicants evaluated the improved cosmetic appearance of a high fipronil formulation with the presence of crystallization inhibitor with various formulations for optimal aesthetics.

The present application provides a formulation of a high concentration of fipronil. The topical veterinary composition is applied to an animal with a hair coat such as a cat or dog. As the solvent evaporates from the composition, a visible residue or deposit forms, especially in formulations with a high concentration of fipronil without crystallization inhibitor.

Example 2

Aesthetic Assessment of High Concentration Fipronil Compositions on Dogs After Administration The aesthetic effect of the compositions of the invention containing a high concentration of fipronil (e.g. 17% w/v) after administration to dogs was compared with a typical composition containing 10% w/v fipronil.

General Protocol

Study: Animals are shampooed during between Day −5 and Day −1 of the study. Animals are briefly combed and then treated on Day 0 per protocol outlined below and observed for aesthetic effect on the hair coat at the site of application over time.

Treatment Administration: Dogs were weighed before or on Day 0 for dosage/pipette size determination. Before treatment administration, dogs were briefly combed. Treatments were applied on Day 0 based on the calculated dose. Each dose was applied by parting the hair and applying the formulation directly onto the skin between the shoulder blades or other appropriate area. Dogs whose weight was above 10 kg and with a white area on the neck may have received the target on two application sites (one on a dark area and one on a white area).

Evaluation: Aesthetic assessment comprised a visual observation of the dog hair coat and was numerically assessed according the following scores:
Presence of Deposit
0=No
1=small amount
2=moderate amount
3=high amount
Oiliness/Wetness
0=No
1=slightly
2=moderate
3=highly
Lackluster/Dryness
0=No
1=slightly
2=moderate
3=highly Quantitative scores for the treatment site were assigned in 0.25 increments on a scale of 0 to 3.

A study was conducted using the methodology above to assess the aesthetic impact of three high concentration fipronil spot-on compositions compared with a spot-on composition containing 10% (w/v) fipronil. Table 3 below describes the compositions tested. The solvent carrier was a mixture of diethyleneglycol monoethyl ether (Transcutol® P) and ethanol.

TABLE 4

| Group | Treatment | Formulation |
|---|---|---|
| 1 | Control 10% w/v fipronil | 5% w/w Polysorbate 80 + 5% polyvinylpyrrolidone |
| 2 | A 17% w/v fipronil | 5% w/v Polysorbate 80 + 5% polyvinylpyrrolidone |
| 3 | B 17% w/v fipronil | 5% Polysorbate 80 + 9% polyvinylpyrrolidone |
| 4 | C 17% w/v fipronil | 7.5% Polysorbate 80 + 7.5% polyvinylpyrrolidone |

Polyvinylpyrrolidone grade used was Kollidon ® 17 sold by BASF

Average scores (n=5) for the control Group and Treatment Groups 2, 3 and 4 (formulations A, B and C) at approximately 6-8 hours post application were 0.6, 1.4, 1.4 and 0.7, respectively. At approximately 22-24 hours post treatment, the average scores were 1.1, 1.5, 1.7 and 1.3, respectively. Treatment C had nearly identical results in terms of aesthetics when compared to the low concentration control. These results confirmed that a reduction of deposit (residue) on the animal's hair coat could was possible for compositions containing a higher concentrations of fipronil.

Example 3

Extent of Deposit on Dogs

A further study was conducted to assess the impact of crystallization inhibitors on composition C in Table 4 compared with a composition with the same concentration of fipronil but without crystallization inhibitors and a control composition having a lower concentration of fipronil (10% w/v). In this second study, the aesthetic assessment was conducted at approximately 4, 8 and 24 hours post administration. At the 4 hour time point, the average aesthetic scores for the lower concentration control (n=7), the composition without crystallization inhibitors (n=7) and test composition C (n=7) were 0, 0.89 and 0.61, respectively. At the 8 hour time point, the average aesthetic scores were 0.07, 1.39 and 0.71, respectively. At 24 hours, the average scores were 0.22, 0.61 and 0.96, respectively. Thus, at 4 and 8 hours the test composition was demonstrated to have lower aesthetic scores than the composition without crystallization inhibitors and was determined to be more aesthetic acceptable. Furthermore, although the average score for the composition without crystallization inhibitors was lower at the 24 hour time point, all groups were found acceptable at this time point. The group administered the composition without crystallization inhibitors was the only group with individual scores of 2 or greater at any observation points.

Example 4

Extent of Deposit on Cats

A further study to assess the aesthetic effect of crystallization inhibitors on spot-on compositions comprising a high concentration of fipronil (17% w/v) on cats. The volume of the composition administered to cats is significantly lower than the volume administered to dogs due to the size of the animal (e.g. 0.4 or 0.5 ml); thus, it is expected that the aesthetic effect of the crystallization inhibitors in the compositions will not be as pronounced as with dogs. Using the same protocol described above, Compositions A and B were tested and compared with a composition without crystallization inhibitor and a lower concentration control (10% w/v fipronil). Aesthetic assessment was conducted at approximately 4, 8 and 24 hours post administration of the spot-on compositions. Average scores (n=4) at the 4 hour time point were 0, 0.75, 0.25 and 0 for the low concentration control, composition without crystallization inhibitor, composition A and composition B, respectively. At the 8 hour time point average scores were 0, 1.0, 0.25 and 0.5, respectively. At the 24 hour time point average scores were 0, 0, 0.75 and 0.5. Although there is some variation, all groups were found to be acceptable. Furthermore, Compositions A and B performed better at the 4 and 8 hour time points. This confirms that the volume of the composition is a significant factor with respect to the aesthetic effect of the compositions.

Example 5

Efficacy of Compositions of the Invention Against Ticks on Dogs

A composition of the invention containing 17% (w/v) fipronil in a carrier containing a combination of polyvinylpyrrolidone and polysorbate 80 as crystallization inhibitor (7.5% w/v of each) in diethyleneglycol monoethyl ether with 10% v/v ethanol was tested for efficacy against *Ixodes*

*ricinus* on dogs compared with an untreated control group in a blinded, randomized study. Both the treatment and control groups contained eight dogs. Dogs were infested with 50 adult, unfed female ticks on days −2, 7, 21, 28, 35 and 42. The treatment group was treated with a spot-on composition to deliver 12 mg/kg fipronil and 6 mg/kg (S)-methoprene on day 0. Ticks were removed and counted 48 hours after each infestation to assess efficacy. In this study, the composition of the invention demonstrated efficacy of greater than 95% or better for at least 30 days versus the control group based on geometric means of counted ticks.

Example 6

Efficacy of Compositions of the Invention against Fleas on Dogs

A composition of the invention containing 17% (w/v) fipronil in a carrier containing a combination of polyvinylpyrrolidone and polysorbate 80 as crystallization inhibitor (7.5% w/v of each) in diethyleneglycol monoethyl ether with 10% v/v ethanol was tested for efficacy against *Ctenocephalides felis* on dogs compared with an untreated control group in a blinded, randomized study. Both the treatment and control group contained eight dogs. Dogs were infested with 100 unfed adult fleas on days −2 and subsequently on days 7, 21, 28, 35 and 42. The treatment group was administered spot-on composition on day 0 to deliver a dose of 12 mg/kg fipronil and 6 mg/kg (S)-methoprene. The dogs were examined on days 2, 9, 23, 30, 37 and 44, 48 hours after each infestation. In this study, the treatment group demonstrated an efficacy of greater than 95% for at least 30 days and an efficacy of greater than 90% for at least 37 days versus an untreated control group based on geometric means of counted live fleas. Although the present invention and its advantages have been described in detail, it should be understood that various changes, substitutions and alterations can be made herein without departing from the spirit and scope of the invention as defined in the appended claims.

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A topical veterinary composition comprising:
   (a) from about 16% to about 18% (w/v) fipronil;
   (b) optionally, about 5% to about 15% (w/w) (S)-methoprene;
   (c) about 14% to 18% (w/v) of a crystallization inhibitor which is a combination of polyvinylpyrrolidone and polyoxyethylene (20) sorbitan monooleate in a weight:weight ratio of about 2:1 to about 1.7:1;
   (d) an organic co-solvent selected from the group consisting of methanol, ethanol, and isopropanol;
   (e) an organic solvent which is butyl diglycol, dipropylene glycol n-butyl ether, ethylene glycol monoethyl ether, ethylene glycol monomethyl ether, dipropylene glycol monomethyl ether, liquid polyoxyethylene glycols, propylene glycol monomethyl ether, propylene glycol monoethyl ether, diethylene glycol monoethyl ether, or any combination thereof; and
   (f) optionally, about 0.01% to about 2.0% of an antioxidant wherein the organic solvent (e) is present in the overall composition in a proportion representing a compliment to 100% of the composition;
   wherein, the organic co-solvent to organic solvent is in a weight:weight ratio of between 1/15 and 1/2; and
   wherein composition results in less than 10 crystals when placed on a glass slide at 20° C. for 24 hours.

2. The topical veterinary composition of claim 1, wherein the organic co-solvent is ethanol.

3. The topical veterinary composition according to claim 1 wherein the antioxidant is BHA or BHT, or a combination thereof.

4. The topical veterinary composition of claim 1, wherein the composition is in the form of a spot-on formulation.

5. A topical veterinary composition comprising:
   (a) from about 16% to about 18% (w/v) fipronil;
   (b) optionally, about 5% to about 15% (w/w) (S)-methoprene;
   (c) about 14% to about 18% (w/v) of a crystallization inhibitor which is a combination of polyvinylpyrrolidone and polyoxyethylene (20) sorbitan monooleate in a weight:weight ratio of about 2:1 to about 1.8:1;
   (d) an organic co-solvent which is ethanol;
   (e) an organic solvent which is diethylene glycol monoethyl ether; and
   (f) optionally, about 0.01% to about 2.0% of an antioxidant wherein the organic solvent (e) is present in the overall composition in a proportion representing the compliment to 100% of the composition;
   wherein, the organic co-solvent to organic solvent is in a weight:weight ratio of between 1/15 and 1/2; and
   wherein composition results in less than 10 crystals when placed on a glass slide at 20° C. for 24 hours.

6. The topical veterinary composition according to claim 5, which comprises about 15% (w/v) of the crystallization inhibitor.

7. The topical veterinary composition according to claim 5, wherein the antioxidant is BHA or BHT, or a combination thereof.

8. The topical veterinary composition of claim 5, wherein the composition is in the form of a spot-on formulation.

* * * * *